United States Patent
Scannell et al.

(10) Patent No.: US 6,300,571 B1
(45) Date of Patent: Oct. 9, 2001

(54) MINERAL-INSULATED SUPPLY LINE

(75) Inventors: Robert Scannell, Mühlstrasse; Annette Kipka, Flughafenstrasse, both of (DE)

(73) Assignee: Heraeus Electro-Nite International N.V. (DE)

( * ) Notice: Subject to any disclaimer, the term of this patent is extended or adjusted under 35 U.S.C. 154(b) by 0 days.

(21) Appl. No.: 09/194,224

(22) PCT Filed: Mar. 17, 1998

(86) PCT No.: PCT/EP98/01528
§ 371 Date: Aug. 2, 1999
§ 102(e) Date: Aug. 2, 1999

(87) PCT Pub. No.: WO98/43076
PCT Pub. Date: Oct. 1, 1998

(30) Foreign Application Priority Data

Mar. 21, 1997 (DE) ............................................ 197 12 026
Feb. 26, 1998 (DE) ............................................ 198 08 030

(51) Int. Cl.⁷ ............................................ H01B 17/58
(52) U.S. Cl. ............... 174/68.1; 174/74 A; 174/110 R; 174/113 R; 174/116; 174/126.4
(58) Field of Search ................... 174/68.1, 79.4, 174/98, 99 R, 110 R, 113 R, 116, 126.4, 137 B, 138 R, 120 R

(56) References Cited

U.S. PATENT DOCUMENTS

| | | | |
|---|---|---|---|
| 3,928,071 | * 12/1975 | Thornton | 136/83 R |
| 4,267,029 | * 5/1981 | Massarsky | 204/196 |
| 4,373,375 | * 2/1983 | Terhune et al. | 73/19 |
| 4,611,604 | * 9/1986 | Botvidsson et al. | 128/784 |
| 4,679,317 | * 7/1987 | Bailleul et al. | 29/828 |
| 4,689,443 | * 8/1987 | Bailleul | 174/102 P |
| 5,156,688 | * 10/1992 | Buhler et al. | 136/211 |
| 5,336,851 | * 8/1994 | Sawada et al. | 174/110 A |
| 5,340,455 | * 8/1994 | Kroon et al. | 204/196 |
| 5,350,638 | * 9/1994 | Sawada et al. | 428/623 |
| 5,467,112 | * 11/1995 | Mitani | 347/1 |
| 5,536,478 | * 7/1996 | Lipp et al. | 422/174 |
| 5,560,851 | * 10/1996 | Thimm et al. | 219/543 |

* cited by examiner

Primary Examiner—Dean A. Reichard
Assistant Examiner—W. David Walkenhorst
(74) Attorney, Agent, or Firm—George H. Gerstman; Seyfarth Shaw

(57) ABSTRACT

The invention relates to a mineral-insulated supply line for a sensor, including a sleeve and at least one internal conductor arranged in the sleeve, with one end of the at least internal conductor connected with a sensor element or its supply line and with the sleeve containing a mineral powder as insulation material. To obtain a high temperature-resistant and corrosion-resistant supply line for gas sensors, at least one internal conductor is made of a metal from the group consisting of tantalum, titanium, niobium, molybdenum, vanadium, zirconium, rhenium, and osmium, or of an alloy based on at least one of these metals.

20 Claims, 2 Drawing Sheets

MINERAL-INSULATED SUPPLY LINE

The invention relates to a mineral-insulated supply line for a sensor, comprising a sleeve and at least one internal conductor arranged in the sleeve, with one end of the internal conductor connected with a sensor element or its supply line and with the sleeve containing a mineral powder as insulation material. The invention relates further to the use of such a supply line.

A wide variety of this type of supply line is known in the art. For example, a mineral-insulated supply line for a temperature sensor is described in DE 43 30 447 A1. This supply line exhibits an internal conductor made of a nickel-chrome alloy material. A similar supply line in which the internal conductor consists of wires made of a precious metal, which are surrounded by a sleeve made of a nickel-chrome or nickel-chrome-iron alloy, is known from DE 69942. Similar supply lines are known from DE 40 22 051 A1 and from U.S. Pat. No. 4,590,669.

These mineral-insulated supply lines are used for resistance thermometers or as thermoelectric cell wires. They utilize a property of the measuring element, whereby its electrical resistance or thermoelectric voltage depends on the temperature of the material.

For purposes of temperature measurement, the conductors described above are operated virtually without current. However, applications for mineral-insulated supply lines with other sensors, such as gas sensors, are becoming increasingly conceivable. Such sensors include sensor elements with supply and discharge lines for current; these sensors are operated live instead of without current. A mineral-insulated supply line in which the internal conductor operates live is known from WO 95/18965. However, this creates problems in connection with the use of known supply lines, as these lines corrode very easily in an energized state, particularly at higher temperatures such as those which predominate in combustion exhaust gases. In addition, these known materials are relatively difficult to mold precisely, as an unwanted elastic effect takes place. As the materials themselves exhibit low conductivity, they become additionally heated by the flow of current. This is also undesirable or disadvantageous.

Consequently, the objective of this invention is to provide a mineral-insulated supply line whose internal conductors are also suitable for use as high temperature-resistant and corrosion-resistant connection materials for sensors, particularly for gas sensors, when in an energized state.

According to the invention, this objective is solved in that at least one internal conductor is made of a metal from the group consisting of tantalum, titanium, niobium, molybdenum, vanadium, zirconium, rhenium, and osmium, or of an alloy based on at least one of these metals. This type of supply line is highly resistant to high temperatures and corrosion, so that, advantageously, it can even be designed and is suitable for use as a supply line for a heater which, if applicable, is surrounded by a gas sensor, and where the supply line is directly exposed to the hot exhaust gas and its corrosive effects. Surprisingly, it has been demonstrated that such internal conductors are also very resistant when in a charged state. If such a heater line (as an anode) is made of titanium, which may be preferable for cost reasons or for reasons of high temperature stability, the second internal conductor (cathode) should preferably be made of a known iron-chrome-nickel alloy. A different material can be selected for the cathode if, for example, tantalum is used as the anode.

For certain applications, it is advantageous for at least one internal conductor to have a coating which is catalytically active for reducing gases, with this coating preferably consisting of a precious metal or precious metal alloy. This coating can serve as a catalyst for reducing gases (hot exhaust gases), especially $H_2$. It is also advantageous for the sleeve to be closed at both ends and only to exhibit openings for the internal conductors, of which there is at least one, so that the insulation material is protected.

According to the invention, the mineral-insulated supply line can be used for a gas sensor for measurement of gaseous components in a gas compound and, especially, as the supply line of a heater of the gas sensor.

BRIEF DESCRIPTION OF THE DRAWINGS

In the following text, a prototype of the invention is explained on the basis of a drawing. In the drawing:

FIG. 1 only depicts the mineral-insulated supply line 1. For reasons of. simplicity, the components that are connected to one another by the mineral-insulated supply line 1, i.e., the analysis electronics and the sensor element, are not shown. However, an individual skilled in the art is sufficiently familiar with these components.

Figure 1:
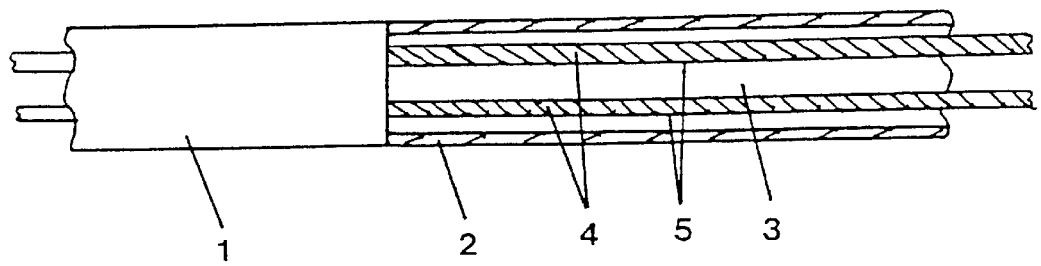
FIG. 1 depicts a partial section through a mineral-insulate supply line.

The mineral-insulated supply line 1 has a sleeve which is made of a conventional material, e.g., Inconel. Several internal conductors 4, which are embedded in an insulation material 3, are arranged inside the sleeve 2. Magnesium oxide or aluminum oxide can, for example, be used as insulation material 3. The internal conductors 4 are made of tantalum. They have a coating 5 of platinum or palladium, which serves as a catalyst for reducing gases. In a further example, the internal conductor acting as a cathode is made of Inconel, while the internal conductor acting as an anode is made of titanium (or of tantalum). As mentioned earlier, at least one sensor element is connected to one side of the internal conductor. Such a sensor element for measurement of the gaseous components of a gas compound exhibits a heater which is connected to an internal conductor 4 (anode-titanium). The internal conductors 4 are charged during the measurement, with a relatively high current flowing through the internal conductor being used as a supply line for the heater. Nevertheless, as the internal conductors are highly resistant and do not corrode, they represent, on the one hand, a reliable connection to the sensor element while also making it possible to achieve reproducible readings over longer periods of time.

The corrosion resistance is demonstrated below on the basis of exemplary tests.

Corrosion test 1

Figure 2:
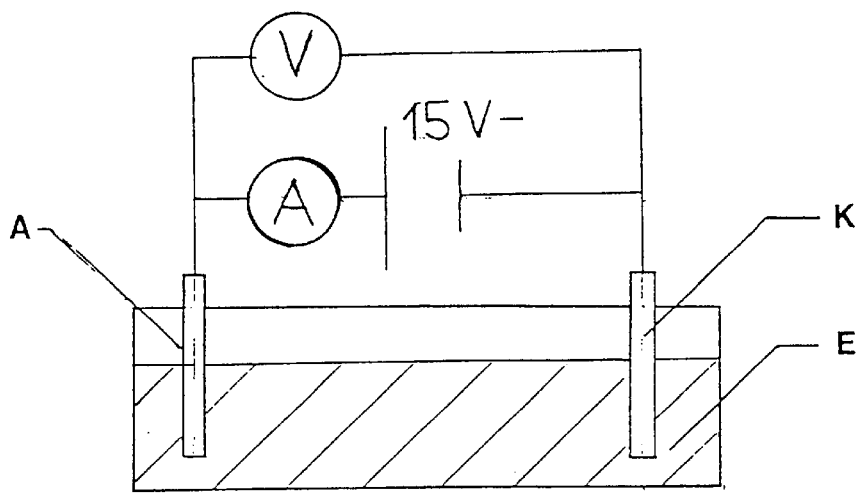
FIG. 2 depicts a setup for a corrosion test.
Figure 3:
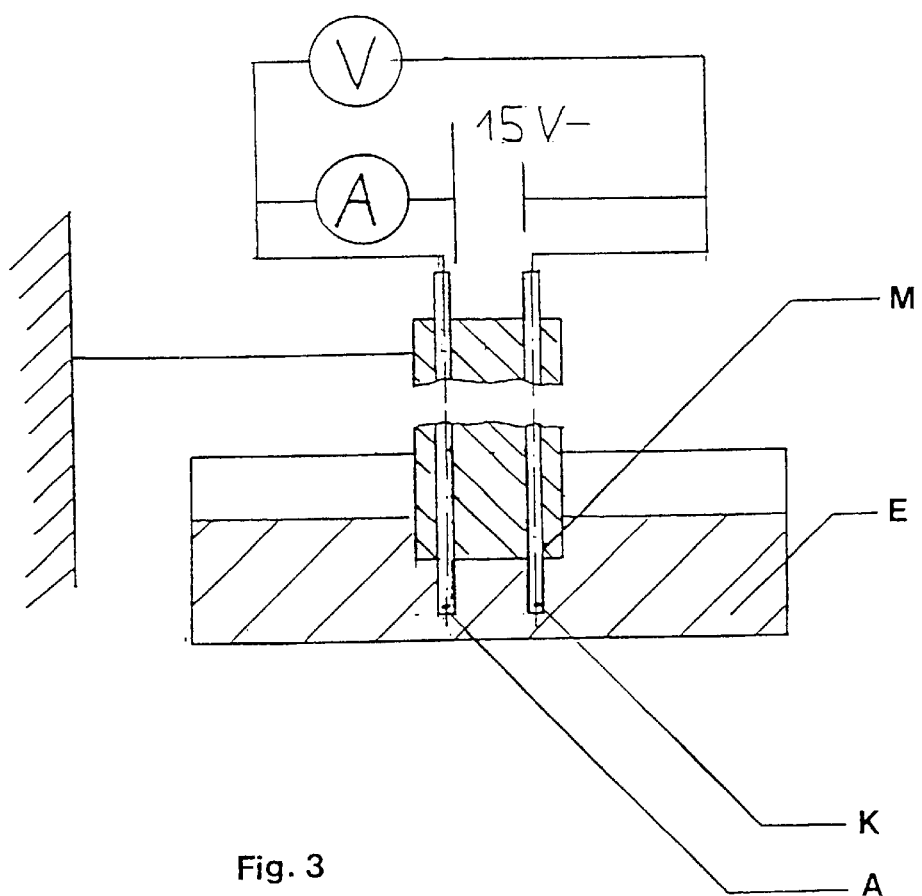
FIG. 3 depicts an additional setup for a corrosion test.

The test was performed in the setup depicted in FIG. 2. The anode A (material to be tested) consists of a wire with a diameter of about 1.5 mm, which was immersed into an electrolyte E. The electrolyte E is made of a synthetic exhaust gas condensate. A platinum wire with a diameter of about 1.5 mm is used as a cathode K. Both the anode A and the cathode K are partially immersed in electrolytes E. Each liter of electrolyte E contains 250 mg of 96% $H_2SO_4$, 250 mg of 37% HCl, 1 g of NaCl, with the remaining consisting of distilled water. The voltage between the anode A and the cathode K is 15 volts. The current flowing between the anode A and the cathode K is measured and represents a measure of anodic disintegration, as current can only flow until the anode A has disintegrated. Table 1 depicts test results for several anode materials. The first materials correspond to the state of the art, while the last two materials (tantalum and titanium) are materials according to the invention.

TABLE 1

| Anode (+) | Cathode (−) | Durability* | Remarks |
|---|---|---|---|
| Inconel (2.4816) | Pt | 20 to 40 minutes | |
| Nisil | Pt | 70 to 120 minutes | Material used in thermoelectric cells |
| CuNi23Mn1 | Pt | 38 minutes | Corrosion-resistant resistance alloy |
| Ta | Pt | >72 hours | Test discontinued, no damage |
| Ti | Pt | >72 hours | Test discontinued, no damage |

*time until disintegration of the anode (I = 0)

As indicated by Table 1, the materials titanium and tantalum are considerably more resistant than the known materials in the environment relevant to the invention.

Corrosion test 2

In contrast to the first corrosion test, the second corrosion test involves a comparison among various mineral-insulated cables. The mineral-insulated cable M has a diameter of about 3.5 mm and contains an anode A with a diameter of about 0.5 mm and a cathode K, which also has a diameter of about 0.5 mm. An electrolyte E is used which has the same composition as in corrosion test 1. The anode A and the cathode K protrude from the moisture-proof closed end of the mineral-insulated cable M; this end of the cable M is immersed in the electrolyte E. As in the first corrosion test, the voltage between the anode A and the cathode K is 15 volts. The current flowing between the anode A and the cathode K is measured and represents a measure for anodic disintegration (corrosion). The first line in Table 2 depicts a test using materials based on the state of the art (Inconel), which were used as both the anode A and the cathode K. The following three lines depict the results of experiments with anode materials according to the invention, with various materials being used as the cathode.

TABLE 2

| Anode (+) | Cathode (−) | Durability* | Remarks |
|---|---|---|---|
| Inconel (2.4816) | Inconel (2.4816) | 13 to 18 minutes | |
| Ta | Ta | >120 minutes | Test discontinued, no damage |
| Ta | Inconel (2.4816) | >120 minutes | Test discontinued, no damage |
| Ti | Inconel (2.4816) | >160 minutes | Test discontinued, no damage |

*time until disintegration of the anode (I = 0)

Based on Table 2, it is evident that mineral-insulated cables M in which the anode is made of a material according to the invention exhibit substantially greater durability and, consequently, greater corrosion resistance than those in which the anode is made of materials known in the art. The durability of the anode A does not appear to be affected or does not appear to be significantly affected by the material used as the cathode K.

What is claimed is:

1. A mineral-insulated supply line for a sensor, comprising a sleeve and at least one internal conductor arranged in the sleeve, with one end of the at least one internal conductor connected with a sensor element or its supply line and with the sleeve containing a mineral powder as insulation material, characterized in that said at least one internal conductor is made of a metal selected from the group consisting of tantalum, niobium, molybdenum, vanadium, zirconium, rhenium, and osmium, or of an alloy based on at least one of these metals.

2. A mineral-insulated supply line according to claim 1, characterized in that the at least one internal conductor has a coating which is catalytically active for reducing gases.

3. The mineral-insulated supply line of claim 2, in which said coating consists essentially of a precious metal or precious metal alloy.

4. A mineral-insulated supply line according to claim 1 characterized in the sleeve is closed at both ends and only exhibits openings for the at least one internal conductor.

5. A mineral-insulated supply line according to claim 1 characterized in that the at least one internal conductor is designed as a supply line for a heater.

6. A method of using a mineral-insulated supply line according to claim 1 to for a gas sensor for measurement of gaseous components in a gas compound.

7. The method of claim 6 in which said mineral-insulated supply line is used as a supply line of the heater of the gas sensor.

8. The mineral-insulated supply line of claim 1, in which said at least one internal conductor has a coating which is catalytically active for reducing gases, and the sleeve is closed at both ends and only exhibits openings for the at least one internal conductor.

9. The mineral-insulated supply line of claim 8 which is used as a supply line for a heater.

10. The mineral-insulated supply line of claim 8 which is used with a gas sensor for measurement of gaseous compounds in a gas.

11. The mineral-insulated supply line of claim 10, used as a supply line of a heater for said gas sensor.

12. The mineral-insulated supply line of claim 8, in which said coating consists essentially of a precious metal or precious metal alloy.

13. The mineral-insulated supply line of claim 1, in which said at least one internal conductor consists essentially of tantalum.

14. The mineral-insulated supply line of claim 13, in which said at least one internal conductor has a coating of platinum or palladium.

15. A mineral-insulated supply line for a sensor, comprising a sleeve and at least one internal conductor arranged in the sleeve, with one end of the internal conductor connected with a sensor element or its supply line and with the sleeve containing a mineral powder as insulation material, characterized in that at least one internal conductor is made of a metal selected from the group consisting of tantalum, titanium, niobium, molybdenum, vanadium, zirconium, rhenium, and osmium, or of an alloy based on at least one of these metals, further in which said at least one internal conductor has a coating which is catalytically active for reducing gases.

16. The mineral-insulated supply line of claim 15, in which said coating consists essentially of a precious metal or precious metal alloy.

17. The mineral-insulated supply line of claim 16, in which said at least one internal conductor consists essentially of tantalum.

18. The mineral-insulated supply line of claim 15 characterized in the sleeve is closed at both ends and only exhibits openings for the at least one internal conductor.

19. The mineral-insulated supply line of claim 15 in which said at least one internal conductor consists essentially of tantalum, having a coating of platinum or palladium.

20. The mineral-insulated supply line of claim 15 which is used as a supply line for a heater of a gas sensor.

* * * * *